United States Patent
Delaney

(10) Patent No.: US 8,613,713 B2
(45) Date of Patent: Dec. 24, 2013

(54) WIRE GUIDE HAVING VARIABLE FLEXIBILITY AND METHOD OF USE THEREOF

(75) Inventor: Kevin L. Delaney, Queensbury, NY (US)

(73) Assignee: Cook Medical Technologies LLC, Bloomington, IN (US)

( * ) Notice: Subject to any disclaimer, the term of this patent is extended or adjusted under 35 U.S.C. 154(b) by 558 days.

(21) Appl. No.: 12/473,711

(22) Filed: May 28, 2009

(65) Prior Publication Data

US 2009/0312747 A1    Dec. 17, 2009

Related U.S. Application Data

(60) Provisional application No. 61/061,198, filed on Jun. 13, 2008.

(51) Int. Cl.
*A61B 5/00* (2006.01)
*A61M 25/00* (2006.01)

(52) U.S. Cl.
USPC ........................................................ 600/585

(58) Field of Classification Search
USPC ................................. 600/585; 604/523–539
See application file for complete search history.

(56) References Cited

U.S. PATENT DOCUMENTS

| | | | |
|---|---|---|---|
| 3,749,086 A * | 7/1973 | Kline et al. | 600/585 |
| 4,215,703 A | 8/1980 | Willson | |
| 4,886,067 A * | 12/1989 | Palermo | 600/434 |
| 5,060,660 A * | 10/1991 | Gambale et al. | 600/585 |
| 5,938,623 A | 8/1999 | Quiachon et al. | |
| 6,183,420 B1 * | 2/2001 | Douk et al. | 600/462 |
| 6,672,338 B1 | 1/2004 | Esashi et al. | |
| 7,182,735 B2 * | 2/2007 | Shireman et al. | 600/585 |
| 2002/0072730 A1 | 6/2002 | McGill et al. | |
| 2003/0199960 A1 | 10/2003 | Paskar | |
| 2004/0260333 A1 | 12/2004 | Dubrul et al. | |
| 2005/0131279 A1 | 6/2005 | Boulais | |
| 2005/0143770 A1 | 6/2005 | Carter et al. | |
| 2006/0064036 A1 | 3/2006 | Osborne et al. | |
| 2006/0217755 A1 | 9/2006 | Eversull et al. | |
| 2007/0005084 A1 | 1/2007 | Clague et al. | |
| 2007/0173757 A1 | 7/2007 | Levine et al. | |
| 2008/0045986 A1 | 2/2008 | To et al. | |

* cited by examiner

*Primary Examiner* — Brian Szmal
*Assistant Examiner* — Megan Leedy
(74) *Attorney, Agent, or Firm* — Brinks Gilson & Lione

(57) ABSTRACT

The present invention generally relates to a medical surgical device and specifically a wire guide for percutaneous placement within a body cavity. The flexibility of the wire guide may be varied while it is in place within the body vessel.

19 Claims, 2 Drawing Sheets

WIRE GUIDE HAVING VARIABLE FLEXIBILITY AND METHOD OF USE THEREOF

RELATED APPLICATIONS

This non-provisional patent application claims priority to U.S. Provisional Patent Application No. 61/061,198, filed Jun. 13, 2008, the contents of which are incorporated by reference in their entirety.

TECHNICAL FIELD

The present invention generally relates to a medical surgical device and specifically a wire guide for percutaneous placement within a body cavity. The flexibility of the wire guide may be varied while it is in place within the body vessel.

BACKGROUND

Wire guides are commonly used in vascular procedures, such as angioplasty procedures, diagnostic and interventional procedures, percutaneous access procedures, or radiological and neuroradiological procedures in general, to introduce a wide variety of medical devices into the vascular system. For example, wire guides are used for advancing intraluminal devices such as stent delivery catheters, balloon dilation catheters, atherectomy catheters, and the like within body lumens. Typically, the wire guide is positioned inside the inner lumen of an introducer catheter. The wire guide is advanced out of the distal end of the introducer catheter into the patient until the distal end of the wire guide reaches the location where the interventional procedure is to be performed. After the wire guide is inserted, another device such as a stent and stent delivery catheter is advanced over the previously introduced wire guide into the patient until the stent delivery catheter is in the desired location. After the stent has been delivered, the stent delivery catheter can then be removed from a patient by retracting the stent delivery catheter back over the wire guide. The wire guide may be left in place after the procedure is completed to ensure easy access if it is required.

Conventional wire guides include an elongated wire core with one or more tapered sections near the distal end to increase flexibility. Generally, a flexible body such as a helical coil or tubular body is disposed about the wire core. The wire core is secured to the flexible body at the distal end. In addition, a torquing means can be provided on the proximal end of the core member to rotate, and thereby steer a wire guide having a curved tip, as it is being advanced through a patient's vascular system.

A major requirement for wire guides and other intraluminal guiding members, is that they have sufficient stiffness to be pushed through the patient's vascular system or other body lumen without kinking. However, they must also be flexible enough to pass through the tortuous passageways without damaging the blood vessel or any other body lumen through which they are advanced. Efforts have been made to improve both the strength and the flexibility of wire guides to make them more suitable for their intended uses, but these two properties tend to be diametrically opposed to one another in that an increase in one usually involves a decrease in the other.

For certain procedures, such as when delivering stents around challenging take-off, tortuosities, or severe angulation, substantially more support and/or vessel straightening is frequently needed from the wire guide. Wire guides have been commercially available for such procedures which provide improved support over conventional wire guides. However, such wire guides are in some instances are so stiff they can damage vessel linings when being advanced.

In other instances, extreme flexibility is required as well. For example, when branched or looped stents are to be delivered to a branched vascular region, it is beneficial to insert the wire guide from the branch where a stent is to be located. However, the stent may need to be introduced and guided from a separate branch. In this situation, the wire guide is inserted into the patient's vascular system near the desired stent location and a grasping device is inserted in the branch from which the stent will be introduced. The wire guide may be advanced back along the branch to provide the grasping device access to the distal end of the wire guide. However, the wire guide should be extremely flexible to allow grasping and manipulation of the wire guide without damaging the tissue around the bifurcation formed by the luminal branch. Further, the wire guide should be extremely kink resistant to avoid damaging the wire guide as it is grasped. After the wire guide is retrieved by the grasping device, the stent may be delivered over the wire guide to the desired location. However, available wire guides are not designed to provide the flexibility required to cross up and over the bifurcation of the luminal branch and yet also provide the stiffness required to aid in the insertion of the stent.

In view of the above, it is apparent that there exists a need for an improved design for a wire guide.

BRIEF SUMMARY

One aspect provides a variable stiffness wire guide. In one embodiment, the wire guide includes a distal tip and a core element extending from the distal tip to a proximal connector. An outer coil is disposed coaxially around the core element and has its distal end attached to the distal tip and its proximal end attached to the proximal connector. An inner coil is disposed coaxially around the core element between the core element and the outer coil. The distal end of the inner coil attaches to the distal tip. A shaft element is disposed proximally of the inner coil between the core element and the outer coil. The distal end of shaft element attaches to the proximal end of the inner coil. The shaft element extends through the proximal connector and is movable axially relative to the proximal connector.

In one embodiment, the wire guide also includes a locking mechanism allowing the axial position of the shaft element to be fixed relative to the proximal connector.

The core element can be formed from stainless steel, a stainless steel alloy, a nickel-titanium alloy or combinations thereof. In one embodiment, the core element has a substantially constant cross-section along its length. In another embodiment, the core element has at least one taper reducing the cross-section of the distal portion relative to the proximal portion.

In one embodiment, a coating is present on at least a portion of the surface of the outer coil. The coating can include a polymer.

In another embodiment, the wire guide includes a distal tip and an outer coil extending from the distal tip to a proximal connector and having its distal end attached to the distal tip and its proximal end attached to the proximal connector. An inner coil is disposed coaxially within the outer coil and has its distal end attached to the distal tip. A shaft element is disposed proximally of the inner coil within the outer coil and has its distal end attached to the proximal end of the inner coil.

The shaft element extends through the proximal connector and is movable axially relative to the proximal connector.

DETAILED DESCRIPTION

In accordance with an embodiment of the present invention, a wire guide system includes a wire guide having a mechanism allowing the flexibility of the wire guide to be variable while the wire guide is in place within a patient's body. As used herein, the term "proximal" refers to a portion of the wire guide closest to a physician when placing a wire guide in the patient, and the term "distal" refers to a portion of the wire guide closest to the end inserted into the patient's body.

Figure 1:
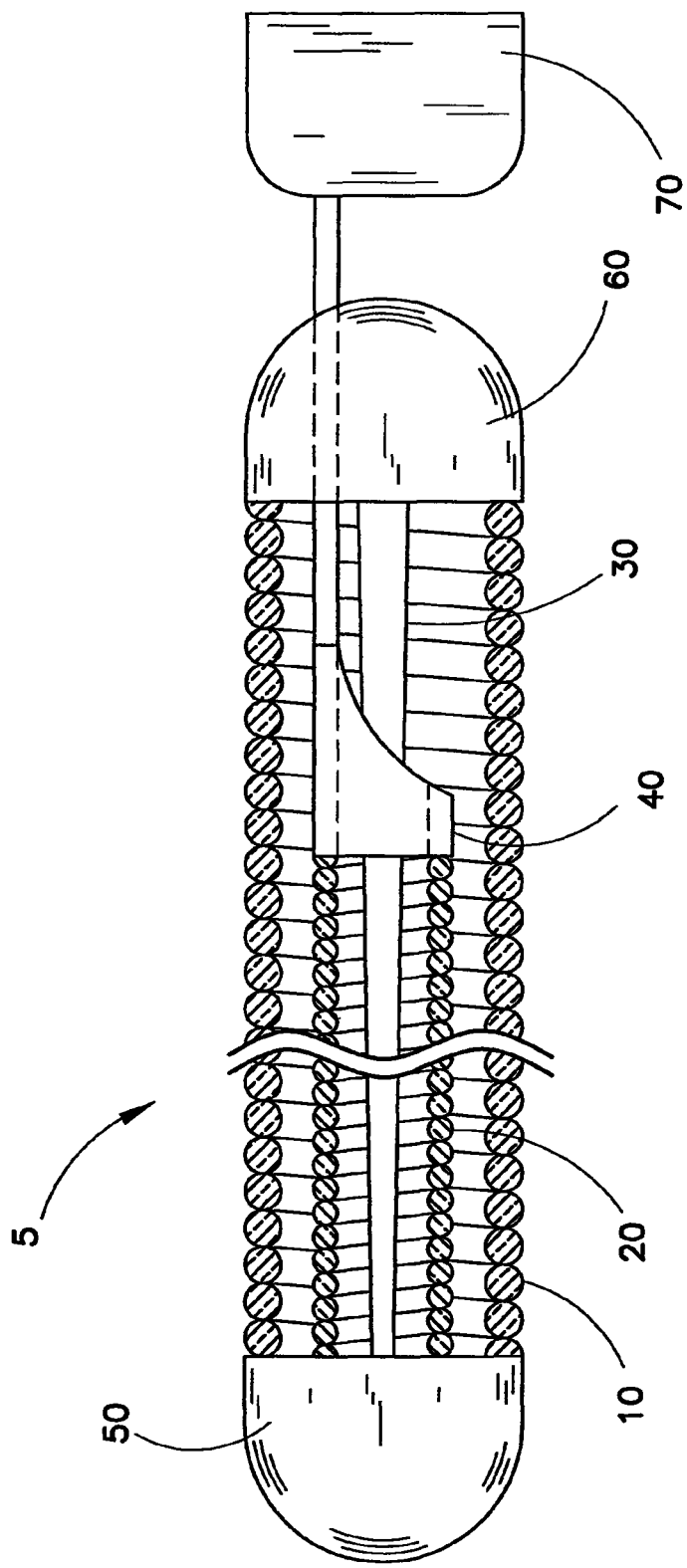
FIG. 1 shows one embodiment of an illustrative wire guide.

Referring now to FIG. 1, this figure illustrates one embodiment of a wire guide 5 incorporating a mechanism allowing for the flexibility of the wire guide to be varied while it is in place within the body of a patient. The wire guide 5 includes a core element 30 extending from a distal tip 50 to a proximal connector 60. Outer coil 10 is disposed coaxially around core element 30 and is attached to distal tip 50 and proximal connector 60.

Inner coil 20 is disposed coaxially around core element 30 between core element 30 and outer coil 10. The distal end of inner coil 20 is attached to distal tip 50. Shaft element 40 is disposed proximally of inner coil 20 between core element 30 and outer coil 10. The distal end of shaft element 40 is attached to the proximal end of inner coil 20. In one embodiment, distal end of shaft element 40 is formed from a cannula. Shaft element 40 extends proximally from its point of attachment to inner coil 10 through proximal connector 60 and is movable axially relative to proximal connector 60. In one embodiment, the proximal end of shaft element 40 connects to handle 70. In other embodiments, wire guide also includes a locking mechanism, such as an Olcott or Hemostat lock (not illustrated), to allow the relative axial positions of shaft element 40 and proximal connector 60 to be fixed.

Figure 2:
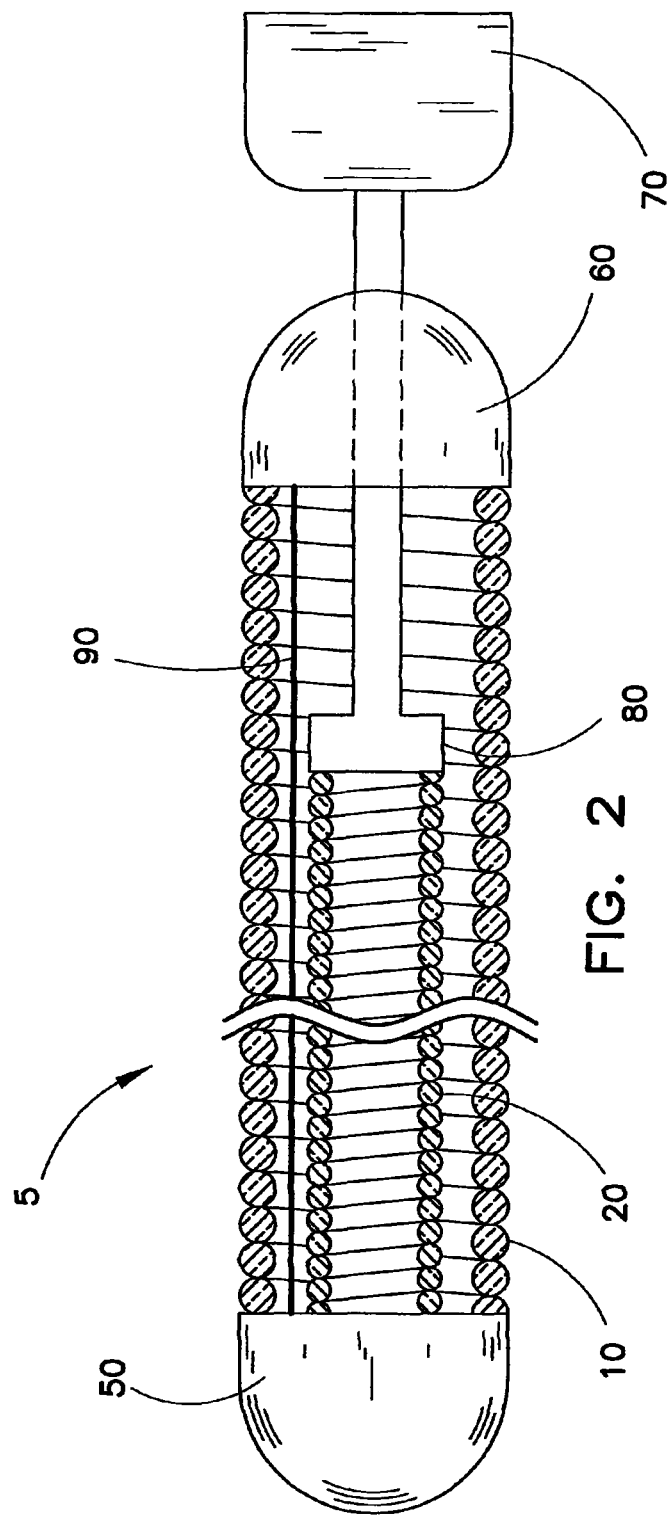
FIG. 2 shows another embodiment of an illustrative wire guide.

Referring now to FIG. 2, this figure illustrates another embodiment of wire guide 5. In this embodiment the wire guide 5 includes outer coil 10 having a distal end attached to distal tip 50 and a proximal end attached to proximal connector 60. Inner coil 20 is disposed coaxially within outer coil 10. The distal end of inner coil 20 is attached to distal tip 50. Shaft element 80 is disposed proximally of inner coil 20 within outer coil 10. The distal end of shaft element 80 is attached to the proximal end of inner coil 20. Shaft element 80 extends proximally from its point of attachment to inner coil 10 through proximal connector 60 and is movable axially relative to proximal connector 60.

In one embodiment, the proximal end of shaft element 80 connects to handle 70. In other embodiments, wire guide also includes a locking mechanism, such as an Olcott or Hemostat lock (not illustrated), to allow the relative axial positions of shaft element 80 and proximal connector 60 to be fixed. In one embodiment, shaft element 80 is formed from a cannula. In other embodiments, shaft element 80 is formed from a solid member.

The guide wire may also include safety wire 90 extending from distal tip 50 to proximal connector 60. Safety wire 90, illustrated in FIG. 2, acts to prevent outer coil 10 from unraveling beyond a maximum length defined by the length of safety wire 90.

The wire guide 5 may have typical wire guide dimensions. The wire guide length may generally be about 90 to about 300 cm, and for use within a patient's coronary system available wire guides are typically about 180 cm in length.

In one embodiment, core element 30 has a cross-sectional area (cross section) that is substantially constant along its length. In other embodiments, the cross-section of core element 30 varies. In one embodiment, the cross-section in the region of the proximal end of core element 30 is greater than is the cross-section in the region of the distal end. In certain embodiments, core element 30 includes at least one taper reducing the cross section in the axial direction of the distal portion relative to that of the proximal portion.

In certain embodiments, core element 30 is manufactured from a material such as stainless steel, a stainless steel alloy, a nickel-titanium alloy, such as nitinol, or combinations of these materials. Inclusion of a radiopaque material, such as platinum or gold, allows for better visibility during manipulation of the wire guide 5 within the body of the patient. In certain embodiments, a radiopaque material is included in other portions of wire guide 5, for example, as part of distal tip, inner coil, outer coil and/or the shaft element.

Core element 30 can be attached to distal tip 50 and/or proximal connector 60 by methods including, but not limited to, adhesive, solder or laser welding. Similar methods can be used to attach inner coil 20 to distal tip 50 and/or proximal connector 60 and outer coil 10 to distal tip 50 and/or the shaft element.

Inner coil 20 and outer coil 10 can be formed from any material suitable for forming expandable springs including, but not limited to stainless steel, alloys including stainless steel, a nickel-titanium alloy, such as nitinol, or combinations of these materials. In one embodiment, inner coil 20 and outer coil 10 are formed from the same material. In other embodiments, they are formed from different materials. In certain embodiments, wire guide 5 further includes a coating on at least a portion of the outer surface of outer coil 10. The coating can include a material that reduces the coefficient of friction on that surface. For example, the coating may include a polymer such as, but not limited to, a fluoropolymer.

In one embodiment, outer coil 10 and inner coil 20 are formed from material having the same or a similar cross-sectional dimension. In other embodiments, they are formed from materials having differing cross-sectional dimensions, for example, the cross-section of one of the coils can be greater or less that the cross-section of the other coil. The cross-section of one or both coils can be constant along the length of the coils. In other embodiments, the cross-section of one or both coils can vary along the length of the coil(s).

In one embodiment, the flexibility of the outer coil and/or the inner coil is constant along the length of the coils. In other embodiments, the flexibility of the outer coil and/or the inner coil varies along the length of the coils. For example, the flexibility of the outer coil and/or the inner coil may be less in the distal region of the wire guide than in the proximal region of the wire guide.

Another aspect provides a method of varying the flexibility of wire guide 5 while it is in place within the body of a patient. Referring again to FIG. 1, as shaft element 40 is moved proximally relative to proximal connector 60, for example, by moving handle 70 in a proximal direction, inner coil 20 tends to increase in length and is prevented in doing so only if distal tip 50 also moves the same distance in a proximal direction. However, any significant axial movement of distal tip 50 relative to proximal connected 60 is prevented by the presence of core element 30 which fixes the relative axial positions of distal tip 50 and proximal connector 60.

As shaft element 40 is moved proximally relative to proximal connector, inner coil 20 is expanded resulting in a decrease in the flexibility of wire guide 5. In certain embodiments, the flexibility of wire guide 5 is decreased over the axial portion defined by the distal and proximal ends of inner coil 20.

Referring again to FIG. 2, as shaft element 80 is moved proximally relative to proximal connector 60, for example, by moving handle 70 in a proximal direction, inner coil 20 tends to increase in length and is prevented in doing so only if distal tip 50 also moves the same distance in a proximal direction. Movement of distal tip 50 in a proximal direction results in compression of outer coil 10, resulting in a decrease in the flexibility of wire guide 5.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A wire guide comprising:
   a distal tip,
   a core element having a proximal connector, wherein a distal end of the core element connects to the distal tip,
   an outer coil disposed coaxially around the core element and having a distal end attached to the distal tip and a proximal end attached to the proximal connector,
   an inner coil disposed coaxially around the core element between the core element and the outer coil, wherein a distal end of the inner coil attaches to the distal tip, and
   a shaft element disposed proximally of the inner coil between the core element and the outer coil, wherein a distal end of the shaft element attaches to a proximal end of the inner coil, wherein the shaft element extends through the proximal connector and is movable axially relative to the distal tip whereby an extension of the inner coil is changed.

2. The wire guide of claim 1, further comprising a locking mechanism allowing the axial position of the shaft element to be fixed relative to the proximal connector.

3. The wire guide of claim 1, wherein the core element comprises a material selected from the group consisting of stainless steel, a stainless steel alloy, a nickel-titanium alloy and combinations thereof.

4. The wire guide of claim 1, the core element having at least one taper reducing a cross-section of a distal portion of the core element relative to a proximal portion of the core element.

5. The wire guide of claim 1, wherein at least one of the outer coil and the inner coil is attached to the distal tip by adhesive, solder or laser welding.

6. The wire guide of claim 1, further comprising a coating on at least one surface of the outer coil.

7. The wire guide of claim 6, wherein the coating reduces the coefficient of friction of the at least one surface.

8. The wire guide of claim 6, wherein the coating comprises a polymer.

9. The wire guide of claim 1, wherein the distal end of the shaft element comprises a cannula.

10. The wire guide of claim 1, wherein at least one of the inner coil and the outer coil comprises stainless steel or a stainless steel alloy.

11. The wire guide of claim 1, wherein the distal tip comprises a radiopaque material.

12. The wire guide of claim 1, having a variable flexibility dependent upon the relative positions of the distal end of the shaft element and the proximal connector.

13. The wire guide of claim 1, wherein the flexibility of the outer coil and the inner coil is constant along the length of the coils.

14. The wire guide of claim 1, wherein the flexibility of at least one of the outer coil and the inner coil varies along the length of the coil.

15. A wire guide comprising:
   a distal tip,
   a proximal connector,
   an outer coil extending from the distal tip to the proximal connector and having a distal end attached to the distal tip and a proximal end attached to the proximal connector,
   an inner coil disposed coaxially within the outer coil, wherein a distal end of the inner coil attaches to the distal tip, and
   a shaft element disposed proximally of the inner coil within the outer coil, wherein a distal end of the shaft element attaches to a proximal end of the inner coil, wherein the shaft element extends through the proximal connector and is movable axially relative to the distal tip whereby an extension of the inner coil is changed.

16. The wire guide of claim 15, wherein at least one of the inner coil and the outer coil comprises stainless steel or a stainless steel alloy.

17. The wire guide of claim 15, further comprising a safety wire extending from the distal tip to the proximal connector.

18. The wire guide of claim 15, further comprising a locking mechanism allowing the axial position of the shaft element to be fixed relative to the proximal connector.

19. A wire guide comprising:
   a distal tip,
   a proximal connector,
   a core element extending from the distal tip to the proximal connector, wherein the core element comprises at least one taper reducing a cross section of a distal portion of the core element relative to a proximal portion of the core element,
   an outer coil disposed coaxially around the core element and having a distal end attached to the distal tip and a proximal end attached to the proximal connector, wherein the outer coil comprises stainless steel or a stainless steel alloy,
   an inner coil disposed coaxially around the core element between the core element and the outer coil, wherein a distal end of the inner coil attaches to the distal tip and wherein the inner coil comprises stainless steel or a stainless steel alloy, and
   a shaft element disposed proximally of the inner coil between the core element and the outer coil, wherein a distal end of the shaft element attaches to a proximal end of the inner coil, wherein the shaft element extends through the proximal connector and is movable axially relative to the distal tip whereby an extension of the inner coil is changed.

* * * * *